United States Patent [19]
Garcia et al.

[11] Patent Number: 5,736,397
[45] Date of Patent: Apr. 7, 1998

[54] METHOD OF USE FOR SEMI-SOLID SHIPPING MEDIUM FOR ORGAN-DERIVED CELLS

[76] Inventors: David B. Garcia; Enrique Chacon, both of 8609 Cross Park Dr., Austin, Tex. 78754

[21] Appl. No.: 783,265

[22] Filed: Jan. 15, 1997

Related U.S. Application Data

[62] Division of Ser. No. 350,963, Dec. 7, 1994, Pat. No. 5,635,344.

[51] Int. Cl.$^6$ ...................................................... A01N 1/02
[52] U.S. Cl. ........................ 435/374; 435/1.1; 435/1.3; 435/404
[58] Field of Search ........................... 435/1.1, 1.3, 374, 435/404

[56] References Cited

U.S. PATENT DOCUMENTS

| | | | |
|---|---|---|---|
| 5,328,821 | 7/1994 | Fisher et al. | 435/1 |
| 5,336,616 | 8/1994 | Liveseg et al. | 435/240.2 |
| 5,635,344 | 6/1997 | Garcia et al. | 435/1.1 |

*Primary Examiner*—Leon B. Lankford, Jr.
*Assistant Examiner*—Deborah K. Ware
*Attorney, Agent, or Firm*—Steven D. Smit

[57] ABSTRACT

A method for the shipment and preservation of organ-derived cells in which the shipping medium is in a firm, substantially congealed state at ambient and chilled temperatures, but becomes substantially fluid upon reaching body temperature. The medium in its fluid state can be poured over cultured cells or tissue slices or used to suspend isolated cells and then can be chilled to reach its congealed state for shipment.

16 Claims, No Drawings

METHOD OF USE FOR SEMI-SOLID SHIPPING MEDIUM FOR ORGAN-DERIVED CELLS

This patent application is a divisional application of application Ser. No. 08/350,963, filed on Dec. 7, 1994, now U.S. Pat. No. 5,653,344.

BACKGROUND OF THE INVENTION

1. Field of the Invention

The present invention relates to a shipping medium for organ-derived living cells, such as cells from the heart, liver, kidney, pancreas, skin and cornea. More specifically, the invention is directed to a method for using semi-solid cell shipping medium, which medium maximizes the viability and protection of organ-derived living cells during temporary storage and transportation.

2. Background Art

Significant medical advances have been made using organ-derived cells as in vitro models of in vivo systems. There are two distinct types of organ-derived cell preparations that are used for research purposes: primary isolated cells and cell lines. Primary isolated cells are cells that are harvested from living organs and are used within hours to a few days of cell harvest. Cell lines, on the other hand, are typically considered as producing continuous cells since they can be subcultured numerous times before the cells die.

A major advantage of using primary isolated cells rather than cell lines is that primary isolated cells provide characteristic biochemical processes that can be observed in vivo. Unfortunately, primary isolated cells from visceral organs such as the heart, liver, and kidney are relatively fragile and have a viability limited to a few days, unless these cells are transformed into cell lines or are cryopreserved. Primary isolated cells that are transformed into cell lines exhibit a proliferative tendency, causing them to more closely resemble cancerous cells than normal cells.

Cryopreservation of organ-derived cells involves a tedious titration of the cells with a cryoprotectant such as dimethylsulfoxide (DMSO), while the temperature is gradually lowered, until an equilibrium is reached across the plasma membrane. The recovery of cells from cryopreservation involves the reverse process followed by immediate removal of DMSO. Unfortunately, recovery of cells from cryopreservation can result in very low cell yields in the range of twenty-five percent to fifty percent.

Therefore, it is desirable to have a preservation medium and\or method to preserve the viability of primary isolated cells in such a manner that the cells closely model the in vivo system, but that minimizes the technical expertise and time required to obtain and preserve such cells.

In addition, it is desirable to have a preservation medium and\or method that not only preserves cells, but allows the efficient banking and shipping of these cells to investigators. The shipping of primary isolated cells of organs, such as cells from the liver, kidney, and heart, remains problematic without cryopreservation when using conventional techniques and storage conditions.

In this regard, the shipment of cells in a preservation medium is fundamentally different from cultivating cells in a conventional growth medium. In the latter case, a nutrient medium containing various cell growth compounds is traditionally used to maintain cells in the same condition as when such cells are in vivo and to encourage life processes, growth and cell proliferation. The continuation of these activities, of course, causes the cells to expend a tremendous amount of energy. The growth medium is usually maintained at a temperature range of 30°–40°C., which is the optimal temperature range for most types of body-derived cells. The growth substrate is usually in a liquid state.

In U.S. Pat. No. 5,336,614 (Soft Agar Assay and Kit), Brown and Schwartz describe an agar-based cell growth formulation that contains a variety of cell growth compounds and that forms a soft gel between 33°–40°C., thereby allowing eukaryotic cells to slowly settle into the gel during culture. Another example of a soft semi-solid growth substrate is Matrigel™, a commercially available growth medium that contains various growth compounds. Matrigel™ is a "reverse-gelling" compound. In other words, it remains fluid at a low temperature, but becomes a soft gel at higher, growth temperatures. A large amount of research has been conducted recently in the use of Extracellular Matrix (ECM) Overlay in which soft gel growth mediums are used to form "sandwiches" by placing a layer of the soft gel both above and below the cells to be cultured to simulate an in vivo environment and to enhance the biochemical activity of the cells. See, e.g., E. Leycluse, et al. (1994) Am. J. Physiol. C1764–C1774; J. S. Sidhu et al., 1994 In Vitro Toxicology (Vol. 4, No. 3) pg. 225, 229; H. G Koebel et al., (1994) Xenobiotica (Vol. 24, No. 2) pg. 95–107; R. Ezzell et al., (1993), Experimental Cell Research 208, 442–452.

In contrast to a growth medium, a shipping medium must be maintained at relatively low temperatures and should be specifically formulated to arrest or suspend cell replication and cellular biochemical processes, thereby conserving energy and cellular integrity.

A fundamental distinction also exists between the preservation and shipment of organ-derived cells and the preservation and shipment of other cells, such as blood cells. The paramount concern in preserving and/or shipping organ-derived cells, such as liver cells, is to preserve the biochemical function of such cells. These cells are biochemically very active, and tend to degrade quickly in a conventional shipping medium, even at low temperatures. In contrast, the preservation and shipment of platelet cells or other blood cells is fairly simple, because these types of cells have no significant biochemical activity.

There have been a number of formulations used for the preservation of blood cells such as red blood cells, leukocytes, and platelet cells. For example, in U.S. Pat. No. 4,476,221 (Protective Solution for Preserving Functional Cells), Kane et al., disclose a red corpuscle preservation solution. In U.S. Pat. No. 4,004,975 (Method of isolation and Cryopreserving Human White Cells from Whole Blood), Lionetti et al. describe a method to cryopreserve blood-derived cells. Tullis, in U.S. Pat. No. 2,786,014 (Platelet Preservation), describes a method to store blood platelet in a sterile soft gelatinous matrix that can be directly injected into humans.

As described above, such preservation formulations are not applicable to the preservation and shipment of organ-derived cells, because of the fundamental differences between organ-derived cells and blood cells.

Some organ-derived cells can be shipped at ambient temperature to above-freezing temperature without cryoprotectant in sealed flasks filled with nutrient medium. However, to minimize agitation that could result in cell injury, the sealed flasks require a large excess of nutrient medium to reduce the airspace in the culture vessel. The use of excess liquid medium, however, does not eliminate potentially harmful movement of the cells, is wasteful, and also increases the weight of the shipment, thereby increasing the shipping costs of the sample.

Additionally, a significant percentage of cell research is conducted in cell culture plates or cell culture wells that cannot be easily sealed. Hence, spillage of the liquid medium results if the container is inverted during shipment. Thus, present technology is lacking in the existence of a medium for shipping cells that maintains cellular viability at ambient to above-freezing conditions, that prevents spillage, that protects the cells being transported and that can be easily used by researchers.

In attempting to overcome some of the problems with preserving organ-derived cells, a variety of preservation formulations and/or methods have been developed. For example, several preservation solutions for the storage of organ tissue intended for transplant have been developed. At present, the most widely used cold organ preservation solution for donor organs is VIASPAN™, disclosed in Belzer et al., U.S. Pat. No. 4,879,283 (Solution for the Preservation of Organs).

Other organ or organ-derived cell preservation solutions and/or methods that have proven useful have been described in the following patents:

Belzer et al., U.S. Pat. No. 4,798,824 (Perfusate for the Preservation of Organs); and Belzer et al., U.S. Pat. No. 4,873,230 (Composition for the Preservation of Organs), (disclosing hydroxyethyl starch as a composition useful in organ preservation solutions);

Andrews, U.S. Pat. No. 5,306,711 (Organ Preservative Solution) (disclosing an organ preservative containing dextran);

Kazumasa et al., U.S. Pat. No. 4,186,253 (Perfusate for Preserving Organ to be Transplanted and Preserving Method) (describing an organ preservation solution that contains a perfluorocarbon compound to increase the oxygen-carrying capacity of an aqueous buffer);

Hurley, et al., U.S. Pat. No. 5,256,571 (Cell Preservative Solution) (describing an acidified alcohol based fixative to preserve the cellular structure of dead cells);

Brockbank, et al., U.S. Pat. No. 5,110,722 (Cell, Tissue or Organ Storage Solution) (describing a method of maintaining cellular viability at about 4° C. or less in a non-frozen state using a physiological buffer containing selenium and transferrin);

Fahy, et al., U.S. Pat. No. 5,217,860 (Method for Preserving Organs for Transplantation by Vitrification);

and U.S. Pat. No. 4,559,298 (Cryopreservation of Biological Materials in a Non-frozen or Vitreous State) (describing methods of cellular preservation by using vitrifiable concentrations of a cryoprotectant);

Swartz, U.S. Pat. No. 4,681,839 (Systems to Preserve Living Tissue) (describing a system to preserve living tissue that has been severed from its host or cells to be stored using a gas permeable bag and a soluble biscuit composed of nutrients); and Jost, U.S. Pat. No. 4,473,552 (Anaerobic Method for Preserving Whole Blood, Tissue, and Components Containing Living Mammalian Cells) (describing a system to preserve living tissue in an oxygen free sealed receptacle). Also of interest is Lemasters and Thurman, U.S. Pat. No. 5,145,771 (Rinse Solution for Organs and Tissues), in which the inventors describe how lethal organ injury occurs after stored organs are perfused with warm physiological buffers and disclose a rinse solution that can be used to flush organs immediately prior to transplant. Specific formula components disclosed in Lemasters et al. are: hydroxyethyl starch (similar to the disclosure in U.S. Pat. Nos. 4,873,230, 4,879,283 and 4,798,824) and adenosine (also disclosed in U.S. Pat. Nos. 4,798,824, 4,920,044, and 5,200,398).

The protective effect of mild acidosis (pH between 6.0 to 7.1) is also described in Lemasters et al. as well as by numerous investigators: Bing, O. H., W. W. Brooks, and J. V. Messer (1973) Science 180, 1297–1298; Pentilia, A. and B. F. Trump (1974) Science 185, 277–278; Bonventre, J. V. and J. Y. Cheung (1985) Am. J. Physiol. 249, C149–C159; and Gores, G. J., K. E. Fleishman, T. E. Dawson, B. Herman, A. L. Nieminen, and J. J. Lemasters (1988) Am. J. Physiol. 255, C315–C322; Koop, A. and H. M. Piper (1992) J. Mol. Cell. Cardiol., 24, 55–65.

Systems customized for the preservation of corneal tissue are described in U.S. Pat. Nos. 4,873,186 (Cornea Storage Medium), 5,104,787 (Method for Apparatus for a Defined Serum Free Medical Solution Useful for Corneal Preservation), and 5,166,048 (Protection of Human Corneal Endothelial Cells).

Although each of the above-described formulations and/or methods are successful in addressing some of the problems associated with the preservation of organ-derived cells, none of these formulations and/or methods are formulated for the shipment of such cells and, hence, they do not solve the significant problems associated with shipping organ-derived cells, such as the problems of rapid cell degradation, physical injury to the cells and spillage.

Thus, no present formulation or method for shipping organ-derived cells exists that adequately arrests biochemical activity and preserves cellular integrity for up to several days, that provides physical protection to organ-derived cells during shipment, that eliminates spillage during shipment and that allows transportation of isolated living cells in a ready-to-use culture apparatus, such as multi-well plates, culture flasks or cover slips.

SUMMARY OF THE INVENTION

It is an object of the present invention to provide a medium and method for the preservation of biochemical activity and viability of organ-derived cells during shipment.

It is a further object of the present invention to provide a medium and method for the preservation of biochemical activity and viability of organ-derived cells during shipment and that preserves said organ-derived cells for a longer period of time than the preservation time achieved when using conventional liquid medium.

It is yet a further object of the present invention to provide a medium and method for the preservation of biochemical activity and viability of organ-derived cells during shipment, that preserves said organ-derived cells for a longer period of time than the preservation time achieved when using conventional liquid medium, and that better physically protects the organ-derived cells during shipment.

It is a further object of the present invention to provide a medium and method for the preservation of biochemical activity and viability of organ-derived cells during shipment, that preserves said organ-derived cells for a longer period of time than the preservation time achieved when using conventional liquid medium, that better physically protects the organ-derived cells during shipment, and that effectively eliminates spillage during shipment.

It is a further object of the present invention to provide a medium and method for the preservation of biochemical activity and viability of organ-derived cells during shipment, that preserves said organ-derived cells for a longer period of time than the preservation time achieved when using conventional liquid medium, that better physically protects the organ-derived cells during shipment, that eliminates spillage during shipment, and that can be easily used by researchers who supply organ-derived cells as well as by researchers who receive the preserved organ-derived cells for experimentation or research.

In furtherance of these objectives and other related objectives, Applicants invention comprises a novel medium for the preservation of biochemical activity and viability of organ-derived cells during shipment, and a method for its use, wherein said medium is in a firm semi-solid property state at ambient and chilled temperatures, but becomes fluid upon reaching human body temperature (37° C.). The novel medium also preserves the biochemical activity and viability of organ-derived cells for a longer period of time than the preservation time achieved when using conventional liquid medium, better physically protects the organ-derived cells during shipment, effectively eliminates spillage during transport, and is easily used by researchers who supply organ derived cells as well as by researchers who receive the preserved organ-derived cells for experimentation or research.

ABBREVIATIONS USED

| CYP 1A1 | Cytochrome P450 isoenzyme 1A1 |
| --- | --- |
| DMSO | Dimethylsulfoxide |
| EROD | Ethoxyresorufin-O-deethylase |
| MOPS | 3-[N-Morpholino]propanesulfonic acid |
| HEPES | N-[2-Hydroxyethyl]piperazine-N'-[2-ethanesulfonic acid] |
| PIPES | Piperazaine-N,N'-bis[2-ethanesulfonic acid] |
| MES | 2-[N-Morpholino]ethanesulfonic acid |
| SOLID | Applicant's Semi-rigid matrix preservation medium |
| LIQUID | Liquid medium storage solution |

BRIEF DESCRIPTION OF THE FIGURES

FIG. 1 compares phase I cytochrome P450 1A1 (CYP 1A1:EROD) metabolic activity of cultured rat hepatocyte cells after cold storage at 4° C. in the present invention (SOLID) with such metabolic activity in typical nutrient medium (LIQUID) at 0, 2 and 3 days.

FIG. 2 compares phase II conjugation potential of cultured rat hepatocyte cells after cold storage at 4° C. in the present invention (SOLID) with such conjugation potential in typical nutrient medium (LIQUID) for 0, 2, and 3 days.

FIG. 3 compares the ratio of phase II conjugation potential to phase I metabolic activity of cultured rat hepatocyte cells after cold storage at 4° C. in the present invention (SOLID) with such ratio in typical nutrient medium (LIQUID) for 0, 2, and 3 days.

DETAILED DESCRIPTION OF PREFERRED EMBODIMENTS OF THE INVENTION

The present invention relates to a shipping medium and method for its use wherein said medium maintains a substantially fluid state at warm temperatures (above 35° C.) and a firm, substantially semi-solid state when chilled (below 25° C.). The principal ingredients of the preferred embodiments will become apparent from Table 1 and from the following description.

The preferred embodiment is a biological matrix comprising one or more of the conventional cell culture nutrient media that are well known in the art, such as Dulbecco's Modified Eagle's Medium, Medium 199, Williams E Medium, Leibovitz Medium or Waymouths Medium. These media are then supplemented with gelatin, glycine or L-alanine, adenosine, dexamethasone, penicillin, and streptomycin, and are buffered at a slightly acidic pH.

The use of glycine, L-alanine and adenosine have been shown to be beneficial against energy depletion. For example, this property of glycine has been described in the following publications: Weinberg, J. M., J. A. Davis, M. Abarzua, and T. Rajan (1987) J. Clin. Invest., 80, 1446–1454; Dickson, R. C., S. F. Bronk, and G. J. Gores (1992) Gastroenterology 102, 2098–2107; Nichols, J. C., S. F. Bronks, R. L. Mellgren, and G. J. Gores (1994) Gastroenterology 106, 168–176, and this property of adenosine has been described in the following publications: Maghill, M. J., M. H. Fox, M. A. Young, K. M. Mullane, D. A. Bullough (1993) Faseb. J., 7, 687; U.S. Pat. No. 5,145,771; U.S. Pat No. 4,873,230; U.S. Pat. No. 4,879,283; U.S. Pat. No. 4,798,824; U.S. Pat. No. 4,798,824; U.S. Pat. No. 4,920,044; and U.S. Pat. No. 5,200,398.

The gelatin provides a media that solidifies to a firm semi-solid when cooled slightly below body temperature, thereby forming a physical barrier of protection around the organ-derived cells and effectively eliminating the risk of spillage during shipping. The use of gelatin to help create a firm semi-solid matrix also provides structural support that promotes a spherical cellular morphology in culture, which aids in preserving biochemical cellular activity, such as liver cell cytochrome P450 activity, during shipment.

Furthermore, under conditions with minimal buffer capacity, the semi-solid property of the matrix provides an environmental gradient buffer surrounding the cell wherein metabolic by-products, such as lactic acid and pyruvic acid, remain in physical proximity to the cell, thereby aiding in the acidification of the immediate environment surrounding each cell. However, a physiological buffer, such as MOPS buffer, is recommended to set and maintain mild acidosis around the cell during shipment.

In an intact organ such as the liver, heart or kidney, collagen is an integral part of the extracellular matrix that is enzymatically removed during the process of cell isolation. Gelatin, which is comprised of water-soluble proteins derived from collagen and which solidifies below 35° C., is, therefore, an ideal constituent of the preferred embodiment of the shipping medium.

Compounds having similar physical and/or biochemical properties to those described above could also be used to supplement the medium. For example, in the place of gelatin, compounds in which the disperse phase combines with the continuous phase to form a firm semi-solid in the temperature range described above could be used, such as xanthan gum, carob cassia, konjac gum, agarose, collagen, or certain other proteins, sugars, hydrocarbons, synthetic polymers and natural polymers. Similarly, depending on the type of the organ-derived cells that are to be shipped, other well-known antibiotics, such as gentamicin, neomycin, nystatin, fungiozone, erythromycin, amphotericin, tetracycline, kanamycin, lincomycin, mitomycin or chloramphenicol, could be used in the place of streptomycin and penicillin to help minimize bacterial cell growth. In addition to using the compounds described above that are part of Applicants' preferred embodiment, a small amount of cyroprotectant, such as dimethylsulfoxide (DMSO), polyethylene glycol or glycerin could be added to the medium to prevent the formation of ice crystals when it is contemplated that the temperature of the medium may fall below freezing.

The preferred embodiment of Applicants' medium is buffered at pH 6.3 using a conventional biological buffer, such as MOPS (3-[N-Morpholino]propanesulfonic acid), HEPES (N-[2-Hydroxy-ethyl]piperazine-N'-[2-ethanesulfonic acid]), imidazole, PIPES (Piperazaine-N, N'-bis[2-ethanesulfonic acid]), or MES (2-[N-Morpholino] ethanesulfonic acid).

TABLE 1

Formulation using:
Waymouths Medium with L-glutamine without sodium bicarbonate

| INGREDIENTS | CONCENTRATION |
| --- | --- |
| Penicillin | 100 U/ml |
| Streptomycin | 100 µg/ml |
| Dexamethasone | 40 µg/ml |
| Adenosine | 0.25 g/L |
| Glycine | 0.15 g/L |
| Gelatin | 30.0 g/L |
| MOPS Buffer (pH 6.3) | 2.0 g/L |

Table 1 discloses a preferred formulation of shipping medium that can be used in many situations. The formulation can be prepared by dissolving in deionized water, the nutrient medium and the various supplements, excluding gelatin. The solution containing the dissolved ingredients is then sterilized by filtration through a 0.2 µm filter. The sterile solution is then heated to approximately 50° C. in an oven. Once the temperature of the solution has equilibrated with the warm external temperature, the solution is transported into a sterile/clean laminar flow hood and sterile gelatin is added. The mixture is then returned to the 50° C. oven and shaken every 5 to 10 minutes until the gelatin has dissolved. The resultant medium can be maintained at 37° C. for immediate use or can be solidified for later use, by placing said medium in cold storage (0°–10° C.). If the medium is solidified by chilling prior to use, the chilled semi-solid medium is liquified by reheating the medium to 37° C.

Once the shipping medium is in a liquified state, cells can be suspended in the medium or the medium can be poured over cells that are attached to the bottom of a cell culture vessel. The depth of the liquified medium that is poured onto the cells should be approximately 0.25–0.50 cm. After the shipping medium has been added to the cells, the product is chilled to 4° C. After several minutes, the liquified medium will solidify and form a relatively hard semi-solid shipping matrix. The resultant semi-solid shipping matrix can then be packaged over ice packs and shipped or can be refrigerated for several days prior to use. The matrix should ideally be maintained in the temperature range of 0°–5° C.

When the cells are ready to be used, the shipping matrix is placed in an incubator or oven for approximately five minutes at 37° C. to liquify the matrix. The liquified shipping medium is then rinsed off or otherwise expelled, and the cells are replenished with conventional nutrient growth medium or a physiological buffer of choice.

EXAMPLE

The Described Semi-Solid Shipping Matrix Preserves Liver Cell Metabolic Capacity During Cold Storage The following example shows the protective effects of the preferred embodiment on liver cell biochemical function, most notably on drug metabolism. Experiments were conducted to determine if the storage medium of the present invention would preserve cellular metabolic viability of cultured rat liver cells. Rat hepatocyte cultures were selected for viability assessment due to their rapid degradation of metabolic enzymes. As an index of metabolic viability, Applicants examined cytochrome P450 1A1 (CYP 1A1) as 7-ethoxyresorufin-O-deethylase (EROD) enzymatic activity using 4 µg/ml 7-ethoxyresorufin, a classical substrate for CYP 1A1. The enzymatic reaction results in the fluorescent product, resorufin.

EROD experiments were conducted in Hank's balanced salt solution containing 350 µg/ml dicumerol to inhibit cytosolic oxidioreductases. Phase II conjugation potential was monitored by inhibiting the cellular re-uptake of resorufin with 0.2 mg/ml salicylamide and measuring total resorufin. The amount of resorufin formed after 2.5 hours of incubation was measured by high performance liquid chromatography using fluorescence detection.

Phase I and Phase II EROD activity was determined from:
1) cells incubated after 4 hours in culture (0 days in culture);
2) cells incubated for 4 hours in culture then stored for 2–3 days at 4° C. in the semi-solid shipping matrix (SOLID); and
3) cells incubated for 4 hours in culture then stored for 2–3 days at 4° C. in liquid nutrient medium (LIQUID). Significant differences observed were determined by analysis of variance and Scheffe's post-hoc test using $P \leq 0.001$.

Phase I EROD activity for cultured rat hepatocyte cells in cold storage for 0, 2, and 3 days are shown in FIG. 1. Hepatocyte cells stored in the semi-solid shipping matrix (SOLID) for 2–3 days showed no significant decrease in CYP 1A1 activity. EROD activity for cells stored in the solid matrix was maintained within 25% of day 0 cultures. Hepatocyte cells stored in liquid medium (LIQUID) showed a significant decrease in CYP 1A1 activity after 2 and 3 days of cold storage. Moreover, hepatocyte cells stored in the semi-solid shipping matrix (SOLID) for 2–3 days had significantly higher levels of EROD activity than those cells stored in the liquid medium (LIQUID).

EROD-dependent Phase II conjugation is shown in FIG. 2. Hepatocyte cells stored in the semi-solid shipping matrix (SOLID) for 2–3 days showed no significant decrease in EROD-dependent phase II conjugation potential. Hepatocyte cells stored in liquid medium (LIQUID) showed a significant decrease in EROD-dependent conjugation after 2 and 3 days of cold storage. Moreover, hepatocyte cells stored in the semi-solid shipping matrix (SOLID) for 2–3 days had significantly higher conjugation potential than cells stored in liquid media (LIQUID). As shown by FIG. 3, Hepatocyte cultures stored in the semi-solid matrix maintained a constant ratio of Phase II conjugation to Phase I metabolism (FIG. 3) over 3 days when compared to the ratio for the cells stored in liquid medium, which showed a six-fold decline.

Although the invention has been described with reference to specific embodiments and examples, these descriptions are not meant to be construed in a limited sense. Various modifications of the disclosed embodiments, as well as alternative embodiments of the invention will become apparent to persons skilled in the art upon the reference to the description of the invention. It is, therefore, contemplated that the appended claims will cover such modifications that fall within the scope of the invention.

We claim:

1. A method for shipping organ-derived cells, which method comprises the steps of: selecting organ-derived cells to be shipped; selecting a biological matrix for the shipment of organ-derived cells, which biological matrix comprises cell preservation medium for preserving organ-derived cells and further comprises a congealing substance in an amount sufficient to cause said biological matrix to be in a substantially fluid state when the temperature of said matrix is about 40° C., to be in a congealed state when the temperature of said matrix is lowered to about 5° C. and to return to a substantially fluid state when the temperature of said matrix is raised to about 40° C.; warming said biological matrix until said biological matrix is in at least a substantially fluid state; covering said selected organ-derived cells with said biological matrix when said biological matrix is in at least a substantially fluid state; and cooling said biological matrix containing said selected organ derived cells until said biological matrix is in at least a substantially congealed state.

2. The method of claim 1 wherein said biological matrix returns to a substantially fluid state when the temperature of said matrix is raised to about 38° C., and wherein said biological matrix further comprises a pH-modifying substance in an amount sufficient to adjust the pH of said biological matrix to a value of from about 6.0 to pH 7.6.

3. The method of claim 2 wherein said biological matrix further comprises an amino acid selected from a group consisting of glycine and L-alanine, wherein the concentration of said amino acid is from 0.02 g per liter to 0.5 g per liter.

4. The method of claim 2 wherein said biological matrix further comprises an amino acid selected from a group consisting of glycine and L-alanine, wherein the concentration of said amino acid is from 0.02 g per liter to 0.5 g per liter.

5. The method of claim 3 wherein said biological matrix further comprises a cyroprotectant in an amount sufficient to substantially prevent the formation of destructive ice crystals in said matrix, when the temperature of said matrix is below 4° C.

6. The method of claim 4 wherein said biological matrix further comprises a cyroprotectant in an amount sufficient to substantially prevent the formation of ice crystals in said matrix, when the temperature of said matrix is below 4° C.

7. The method of claim 3 wherein said biological matrix further comprises adenosine in a concentration of from 0.002 g per liter to 0.5 g per liter.

8. The method of claim 4 wherein said biological matrix further comprises adenosine in a concentration of from 0.002 g per liter to 0.5 g per liter.

9. The method of claim 5 wherein said biological matrix further comprises adenosine in a concentration of from 0.002 g per liter to 0.5 g per liter.

10. The method of claim 6 wherein said biological matrix further comprises adenosine in a concentration of from 0.002 g per liter to 0.5 g per liter.

11. The method of claim 5 wherein said cyroprotectant compound is selected from a group consisting of dimethylsulfoxide, polyethylene glycol, propylene glycol and glycerol.

12. The method of claim 6 wherein said cyroprotectant compound is selected from a group consisting of dimethylsulfoxide, polyethylene glycol and glycerol.

13. The method of claim 11, wherein said congealing substance is selected from a group consisting of gelatin, xanthan gum, carob cassia, konjac gum, agarose and cellulose.

14. The method of claim 12, wherein said congealing substance is selected from a group consisting of gelatin, xanthan gum, carob cassia, konjac gum, agarose and cellulose.

15. A method for shipping organ-derived cells, which method comprises the steps of: selecting organ-derived cells to be shipped; selecting a biological matrix for the shipment of organ derived cells, which biological matrix comprises cell preservation medium for preserving organ-derived cells, 0.1 g/L–1.0 g/L Adenosine, 0.05 g/L–0.5 g\L Glycine, a congealing substance in an amount sufficient to cause said biological matrix to be in a substantially fluid state when the temperature of said matrix is about 40° C., to be in a congealed state when the temperature of said matrix is lowered to about 5° C. and to return to a substantially fluid state when the temperature of said matrix is raised to about 40° C.; an antibiotic compound in sufficient concentration to inhibit bacterial growth in said biological matrix during shipment and a pH-modifying substance in an amount sufficient to adjust the pH of said biological matrix to a value of from 6.0 to pH 7.6; warming said biological matrix until said biological matrix is in at least a substantially fluid state; covering said selected organ-derived cells with said biological matrix when said biological matrix is in at least a substantially fluid state; and cooling said biological matrix containing said selected organ derived cells until said biological matrix is in at least a substantially congealed state.

16. The method of claim 15 wherein said biological matrix further comprises Dexamethasone in a concentration of 10–60 µg/ml.

* * * * *